United States Patent [19]

Maezawa et al.

[11] Patent Number: 5,084,585

[45] Date of Patent: Jan. 28, 1992

[54] PROCESS FOR PREPARATION OF ALUMINOXANE

[75] Inventors: Hiroshi Maezawa; Norio Tomotsu, both of Ichihara, Japan

[73] Assignee: Idemitsu Kosan Company Limited, Tokyo, Japan

[21] Appl. No.: 639,002

[22] Filed: Jan. 9, 1991

Related U.S. Application Data

[63] Continuation of Ser. No. 471,865, Jan. 29, 1990.

[30] Foreign Application Priority Data

Feb. 16, 1989 [JP] Japan .................................. 1-35149

[51] Int. Cl.⁵ .............................................. C07F 5/06
[52] U.S. Cl. .................................................. 556/179
[58] Field of Search ........................................ 556/179

[56] References Cited

U.S. PATENT DOCUMENTS 4,730,072 3/1988 Schoenthal et al. ............... 556/179
4,772,736 9/1988 Edwards ............................ 556/179

FOREIGN PATENT DOCUMENTS 59-95292 6/1984 Japan .
62-36390 2/1987 Japan .

OTHER PUBLICATIONS

W. Kaminsky et al.: "Transition metals and organometallics as catalysts for olefin polymerization", Proceedings of an international symposium, Hamburg, 21st–24th Sep. 1987, pp. 257–268; H. Sinn et al.: Some new results on methyl-aluminoxane, * p. 261, paragraph 2 *.

Primary Examiner—Arthur C. Prescott
Attorney, Agent, or Firm—Frishauf, Holtz, Goodman & Woodward

[57] ABSTRACT

The present invention relates to a process for preparing aluminoxane which comprises reacting an organoaluminum compound and water in a solvent system containing solvent having a higher boiling point than that of the organoaluminum compound, or reacting an organoaluminum compound and water, and then adding a solvent system containing the solvent having a higher boiling point than that of the organoaluminum compound to the reaction mixture; and thereafter condensing the resulting reaction mixture under atmospheric pressure or reduced pressure.

22 Claims, No Drawings

PROCESS FOR PREPARATION OF ALUMINOXANE

This is a continuation of application Ser. No. 07/471,865 filed Jan. 29, 1990.

BACKGROUND OF THE INVENTION

The present invention relates to a process for preparation of aluminoxane, and more particularly to a process for preparing in a simplified manner high purity and high active aluminoxane which is suitable as a catalyst component for production of olefin polymers, styrene-based polymers and so on.

A process for production of olefin polymers or styrene-based polymers by polymerization of olefins or styrene in the presence of a catalyst comprising (A) a transition metal compound and (B) aluminoxane has heretofore been known (Japanese Patent Application Laid-Open Nos. 36390/1987, 95292/1984, etc.).

In accordance with the process disclosed in Japanese Patent Application Laid-Open No. 36390/1987, in preparation of the above aluminoxane, a filtrate obtained by filtering off a solid material from a condensation reaction mixture of an organoaluminum compound and water is allowed to stand, and in the process disclosed in Japanese Patent Application Laid-Open No. 95292/1984, a solvent having a lower boiling point than the starting material of organoaluminum compound, such as toluene or heptane is merely distilled away at room temperature.

The reaction mixture contains an unreacted organoaluminum compound ineffective as a catalyst component along with chain or cyclic aluminoxane. If aluminoxane is prepared in a low boiling point solvent as described above, even after separation of the solvent, the unreacted organoaluminum compound remains undistilled away and pure aluminoxane cannot be obtained.

The present inventors have already proposed a process for obtaining pure aluminoxane in which the unreacted organoaluminum compound is removed by condensing a filtrate after reaction of the organoaluminum compound and water and, thereafter, heat treatment is applied under atmospheric pressure or reduced pressure (Japanese Patent Application No. 66910/1988).

In this process, however, since aluminoxane is obtained as a viscous liquid or a glassy uneven solid at an intermediate stage of heat treatment under reduced pressure, it is difficult to apply uniform heat treatment on an industrial scale and, therefore, an unreacted organoaluminum compound cannot be completely removed.

In utilization as a catalyst of the aluminoxane obtained by the above process, a step to dissolve the aluminoxane in a suitable hydrocarbon solvent or to prepare a slurry containing the aluminoxane is needed, which is undesirable for its commercial practice.

Although aluminoxane is expensive as a catalyst component, high purity aluminoxane has not been obtained as described above. Low purity aluminoxane has a disadvantage of being poor in catalytic activity when used as a catalyst component in production of olefin polymers or styrene-based polymers.

SUMMARY OF THE INVENTION

The present invention is intended to overcome the prior art problems, and an object of the present invention is to provide a process for producing in a simplified manner high purity and high activity aluminoxane which is suitable as a catalyst for production of olefin-based polymers or styrene-based polymers.

The present invention relates to a process for preparing aluminoxane which comprises reacting an organoaluminum compound and water in a solvent system containing solvent having a higher boiling point than that of the organoaluminum compound and then condensing the resulting solution under atmospheric pressure or under reduced pressure. This process is hereinafter referred to as "Process I".

The present invention further relates to a process for preparing aluminoxane which comprises reacting an organoaluminum compound and water, adding thereto a solvent system containing solvent having a higher boiling point than that of the organoaluminum compound, and condensing the resulting solution under atmospheric pressure or under reduced pressure. This process is hereinafter referred to as "Process II".

DETAILED DESCRIPTION OF THE INVENTION

In the Process I, an organoaluminum compound and water are used as starting materials.

As the organoaluminum compound, an organic compound represented by the general formula: $AlR^1_3$ (wherein $R^1$ is an alkyl group having 1 to 8 carbon atoms) is usually used. Specific examples are trimethylaluminum, triethylaluminum, and triisobutylaluminum. Of these, trimethylaluminum is particularly preferred.

As the water to be reacted with the above organoaluminum compound, as well as the usual water, water or various water-containing compounds, solvent saturated water, water adsorbed on inorganic material, and metal salt-containing crystal water such as copper sulfate pentahydrate ($CuSO_4.5H_2O$), and the like can be used.

In the Process I, the above organoaluminum compound and water are reacted in a solvent system containing solvent having a higher boiling point than that of the organoaluminum compound.

The solvent system in the present invention at least contains solvent having a higher boiling point than that of the organoaluminum compound.

As the such solvent, any of aromatic hydrocarbons such as xylene, ethylbenzene, propylbenzene and cumene, and aliphatic hydrocarbons such as octane, nonane and decane can be used as long as it has a higher boiling point than that of the above organoaluminum compound. Preferred are aromatic hydrocarbons having a higher boiling point than that of the above organoaluminum compound.

More specifically, when trimethylaluminum is used as the organoaluminum compound, ethylbenzene, p-xylene, m-xylene, o-xylene, a mixture of the above xylenes, propylbenzene, or cumene, for example, is used as the such solvent.

The solvent system may be a mixture of a solvent having a higher boiling point than that of the above organoaluminum compound and a solvent having a lower boiling point than that of the above organoaluminum compound.

In this case, the proportion of a solvent having a higher boiling point than that of the organoaluminum compound is not less than 10% by weight, preferably not less than 30% by weight, more preferably not less than 40% by weight.

If the proportion of a solvent having a higher boiling point than that of the organoaluminum compound is less than 10% by weight, it is not possible to remove the organoaluminum compound in the subsequent distillation step.

As the solvent having a lower boiling point than that of the organoaluminum compound, aromatic hydrocarbons such as benzene, toluene and the like, and aliphatic hydrocarbons such as hexane, heptane and the like can be used as long as it has a lower boiling point than that of the organoaluminum compound.

The reaction in the solvent is not critical and can be carried out by the known procedure. For example, (1) a method in which an organoaluminum compound is dissolved in a solvent and the resulting solution is contacted with water, (2) a method in which crystal water contained in a metal salt or water adsorbed on an inorganic or organic compound is reacted with an organoaluminum compound in a solvent, and so forth can be employed.

Reaction conditions are not critical; the reaction can be carried out under the usual conditions.

In the Process I, the solution thus obtained is condensed under atmospheric pressure or under reduced pressure If necessary, depending on the preparation method, a solid residue such as a water-containing compound may be previously removed by filtration.

In the Process I, the solution resulting from the reaction (reaction mixture) is condensed, as such or after separation of a solid residue by filtration as described above, under atmospheric pressure or reduced pressure until the weight of the resulting solution is 1/1.5 to 1/100, preferably ½ to 1/10 of the initial weight. In this treatment, although the temperature and pressure vary with the type of the organoaluminum compound or solvent, the temperature is in the range of −30° C. to 200° C. and the pressure is in the range of 760 to 0.01 mmHg.

At this step, however, merely condensation is carried out. If the solvent is thoroughly distilled away; that is, the solution is evaporated to dryness, the resulting solids should be ground and dissolved at the time of use, which makes the procedure complicated.

In this condensation treatment, an unreacted organoaluminum compound ineffective as a catalyst component is distilled away at an earlier stage of the treatment. Thus a high purity aluminoxane solution can be obtained.

In the Process II, a solution obtained by reacting an organoaluminum compound and water is used as a feed solution.

This feed solution may be prepared from the same organoaluminum compound and water as described above by any desired method, and is a solution of a mixture of aluminoxane and an unreacted organoaluminum compound. The solvent to be used in this reaction is not critical; solvents usually used in preparation of aluminoxane from an organoaluminum compound and water can be used.

In the Process II, to a solution of a mixture of aluminoxane and an unreacted organoaluminum compound, a solvent system containing solvent having a higher boiling point than the organoaluminum compound is added.

As the solvent to be added (hereinafter sometimes referred to as an "additional solvent"), the same solvents as listed in the Process I, that is, aromatic hydrocarbons or aliphatic hydrocarbons, preferably aromatic hydrocarbons, having a higher boiling point than the organoaluminum compound can be used. The solvent system may be a mixture of a solvent having a higher boiling point than that of the organoaluminum compound and a solvent having a lower boiling point than that of the organoaluminum compound as same as in Process I.

In the Process II, a solution resulting from addition of the above solvent is condensed under atmospheric pressure or reduced pressure.

In connection with the degree of condensation, the condensation treatment is carried out in the same manner as in the Process I; that is, condensation is carried out under atmospheric pressure or reduced pressure until the weight of the solution becomes 1/1.5 to 1/100, preferably ½ to 1/10 of the initial weight. In this condensation treatment, the temperature and time vary with the type of the organoaluminum compound or solvent; usually the temperature is in the range of −30° C. to 200° C. and the pressure is in the range of 760 to 0.01 mmHg.

If, however, the solvent is thoroughly distilled away; that is, the solution is evaporated to dryness, as described in the condensation treatment of the Process I, the resulting solid residue should be ground and dissolved at the time of use, which makes the procedure complicated. Since the unreacted organoaluminum compound ineffective as a catalyst component is distilled away at an earlier stage of the condensation treatment, it suffices that the condensation is carried out in such a manner that the solution is not evaporated to dryness, taking into consideration the type and amount of the solvent for the feed solution or the additional solvent.

This condensation treatment provides a solution of high purity aluminoxane.

The aluminoxane thus obtained can be used as such, that is, in the form of solution as a catalyst component in combination with a transition metal compound for production of olefin-based polymers such as polyethylene, atactic polypropylene, isotactic polypropylene, polybutene-1 and poly(4-methylpentene-1), an ethylene-propylene copolymer; styrene-based polymers, more specifically styrene-based polymers having a syndiotactic configuration, and further for low degree polymerization of propylene. The above transition metal compound is chosen from the transition metals of Group IVB of the Periodic Table, depending on the type of the objective polymer.

In accordance with the process of the present invention, high purity and high activity aluminoxane can be produced in a simplified manner.

Moreover, a solution of high purity aluminoxane obtained by the process of the present invention can be used as such as a catalyst component for production of olefin-based polymers and styrene-based polymers and thus it does not need a step of dissolving or preparing a slurry.

Accordingly the present invention can be effectively utilized in production of olefin-based polymers and styrene-based polymers.

The present invention is described in greater detail with reference to the following examples.

EXAMPLE 1

(1) Preparation of Aluminoxane

In a 1,000-milliliter autoclave equipped with a wet flow meter in a vent line, 47.4 g (190 mmol) of cupper sulfate pentahydrate (CuSO$_4$.5H$_2$O) and 300 ml of ethylbenzene (boiling point 136° C.) were placed in a nitrogen atmosphere, and after cooling to 0° C., a solution of 48 ml (0.50 mol) of trimethylaluminum (boiling point 126° C.) in 52 ml of ethylbenzene was dropped over 10 minutes. Then the resulting solution was heated to 40° C. over 20 minutes, and the reaction was conducted until 26.8 l of (1.10 mol, 24° C.) was generated. The total reaction time was 8 hours and 33 minutes. After the completion of the reaction, a solid residue was removed by filtration, and 310 g of the filtrate thus obtained was placed in a 500-milliliter glass vessel which could be reduced in pressure and condensed to 100 g under a reduced pressure of 4 Torr while stirring. An elemental analysis and a $^1$H-NMR analysis confirmed that 4.22 g (59 mmol) of trimethylaluminum was dissolved in the distillate. The concentration of aluminum in the condensed solution was 1.6 gram atom/l.

This solution was used as such as a catalyst solution for a polymerization reaction.

(2) Polymerization of Ethylene

In a 1-liter autoclave the atmosphere of which had been replaced with nitrogen, 400 ml of toluene, 1 mmol as an aluminum atom of methylaluminoxane obtained in (1) above and 5 μmol of of biscyclopentadienylzirconium dichloride were placed in this order, and then heated to 80° C. Then, ethylene was continuously introduced into the autoclave and the polymerization reaction was conducted at 8 kg/cm$^2$ for one hour. After the completion of the reaction, methanol was added to decompose the catalyst, and the reaction product was dried to obtain 121 g of polyethylene. Polymerization activity was 265 kg/g.Zr.

(3) Polymerization of Styrene

In a 1-liter autoclave the atmosphere of which had been replaced with nitrogen, 400 ml of styrene, 4 mmol of triisobutylaluminum, 4 mmol as an aluminum atom of methylaluminoxane obtained in (1) above, and 20 μmol of pentamethylcyclopentadienyltitanium trimethoxide were placed and polymerization was conducted at 70° C. for one hour. After the completion of the reaction, the reaction product was washed with a mixture of hydrochloric acid and methanol to remove the catalyst components and then dried to obtain 90.9 g of a polymer. Polymerization activity was 94.9 kg/g.Ti. Syndiotacticity in racemipentad of the polymer as determined by a $^{13}$C-NMR analysis was 97%. The results are shown in Table 1.

EXAMPLE 2

(1) Preparation of Aluminoxane

Aluminoxane (methylaluminoxane) was prepared in the same manner as in Example 1 (1) except that para-xylene (boiling point 138° C.) was used in place of ethylbenzene.

(2) Polymerization of Ethylene

Ethylene was polymerized in the same manner as in Example 1 (2) except that methylaluminoxane obtained in (1) above was used as the aluminoxane. As a result, 129 g of polyethylene was obtained. Polymerization activity was 283 kg/g.Zr.

(3) Polymerization of Styrene

Styrene was polymerized in the same manner as in Example 1 (3) except that methylaluminoxane obtained in (1) above was used as the aluminoxane. As a result, 93.1 g of a polymer was obtained. Polymerization activity was 97.2 kg/g.Ti. Syndiotacticity in racemi pentad of the polymer as determined by a $^{13}$C-NMR analysis was 98%. The results are shown in Table 1.

EXAMPLE 3

(1) Preparation of Aluminoxane

Aluminoxane (methylaluminoxane) was prepared in the same manner as in Example 1 (1) except that xylene (boiling point 137° to 144° C.) was used in place of ethylbenzene.

(2) Polymerization of Ethylene

Ethylene was polymerized in the same manner as in Example 1 (2) except that methylaluminoxane obtained in (1) above was used as the aluminoxane. As a result, 130 of polyethylene was obtained. Polymerization activity was 285 kg/g.Zr.

(3) Polymerization of Styrene

Styrene was polymerized in the same manner as in Example 1 (3) except that methylaluminoxane obtained in (1) above was used as the aluminoxane. As a result, 92.6 g of a polymer was obtained. Polymerization activity was 96.7 kg/g.Ti. Syndiotacticity in racemi pentad of the polymer as determined by a $^{13}$C-NMR analysis was 98%. The results are shown in Table 1.

EXAMPLE 4

(1) Preparation of Aluminoxane

Aluminoxane (methylaluminoxane) was prepared in the same manner as in Example 1 (1) except that isopropylbenzene (boiling point 152° C.) was used in place of ethylbenzene.

(2) Polymerization of Ethylene

Ethylene was polymerized in the same manner as in Example 1 (2) except that methylaluminoxane obtained in (1) above was used as the aluminoxane. As a result, 138 g of polyethylene was obtained. Polymerization activity was 303 kg/g.Zr.

POLYMERIZATION OF STYRENE

Styrene was polymerized in the same manner as in Example 1 (3) except that methylaluminoxane obtained in (1) above was used as the aluminoxane. As a result, 93.5 g of a polymer was obtained. Polymerization activity was 97.6 kg/g.Ti. Syndiotacticity in racemi pentad of the polymer as determined by a $^{13}$C-NMR analysis was 98%. The results are shown in Table 1.

COMPARATIVE EXAMPLE 1

Preparation of Akluminoxane

Aluminoxane (methylaluminoxane) was prepared in the same manner as in Example 1 (1) except that toluene (boiling point 111° C.) was used in place of ethylbenzene.

(2) Polymerization of Ethylene

Ethylene was polymerized in the same manner as in Example 1 (2) except that methylaluminoxane obtained in (1) above was used as the aluminoxane. As a result, 90 g of polyethylene was obtained. Polymerization activity was 197 kg/g.Zr.

(3) Polymerization of Styrene

Styrene was polymerized in the same manner as in Example 1 (3) except that methylaluminoxane obtained in (1) above was used as the aluminoxane. As a result, 17.9 g of a polymer was obtained. Polymerization activity was 18.7 kg/g.Ti. Syndiotacticity in racemi pentad of the polymer as determined by a $^{13}$C-NMR analysis was 96%. The results are shown in Table 1.

TABLE 1

| | Solvent | | | Yield of Polyethylene (g) | Polyethylene Activity (kg/g · Zr) | Yield of SPS* (g) | SPS* Activity (kg/g · Ti) | Tacticity (%) |
| --- | --- | --- | --- | --- | --- | --- | --- | --- |
| | Type | Boiling Point (°C.) | | | | | | |
| Example 1 | Ethylbenzene | 136 | | 121 | 265 | 90.9 | 94.9 | 97 |
| Example 2 | p-Xylene | 138 | | 129 | 283 | 93.1 | 97.2 | 98 |
| Example 3 | Xylene | 137–144 | | 130 | 285 | 92.6 | 96.7 | 98 |
| Example 4 | Isopropylbenzene | 152 | | 138 | 303 | 93.5 | 97.6 | 98 |
| Comparative Example 1 | Toluene | 111 | | 90 | 197 | 17.9 | 18.7 | 96 |

*SPS: Syndiotactic polystyrene

EXAMPLE 5

(1) Preparation of Aluminoxane

In a 1,000-milliliter autoclave equipped with a wet flow meter in a vent line, 47.4 g (190 mmol) of cupper sulfate pentahydrate (CuSO$_4$.5H$_2$O) and 300 ml of toluene were placed, and after cooling to 0° C., a solution of 48 ml of trimethylaluminum (boiling point 126° C.) in 52 ml of toluene was dropped over 10 minutes. Then, the temperature was raised to 40° C. over 20 minutes, and the reaction was carried out until 26.8 l (1.10 mol, 24° C.) of methane gas was generated. After the completion of the reaction, 340 ml of a filtrate obtained by removing a solid residue by filtration and 1,020 ml of ethylbenzene (boiling point 136° C.) as an additional solvent were placed in a 2-liter glass vessel which could be reduced in pressure, and the resulting mixture was condensed to 170 ml under a reduced pressure of 4 Torr while stirring. An elemental analysis and a $^1$H-NMR analysis confirmed that the distillate contained 3.86 g (54 mmol) of trimethylaluminum. The concentration of aluminum in the condensed solution was 1.2 g atom/l. This solution was used as such in a polymerization reaction.

(2) Polymerization of Ethylene

Ethylene was polymerized in the same manner as in Example 1 (2) except that methylaluminoxane obtained in (1) above was used as the aluminoxane. As a result, 109 g of polyethylene was obtained. Polymerization activity was 239 kg/g.Zr.

(3) Polymerization of Styrene

Styrene was polymerized in the same manner as in Example 1 (3) except that methylaluminoxane was used as the aluminoxane. As a result, 86.7 g of a polymer was obtained. Polymerization activity was 90.5 kg/g.Ti. Syndiotacticity in racemi pentad of the polymer as determined by a $^{13}$C-NMR analysis was 97%. The results are shown in Table 2.

EXAMPLE 6

(1) Preparation of Aluminoxane

Aluminoxane (methylaluminoxane) was prepared in the same manner as in Example 5 (1) except that as the additional solvent, para-xylene (boiling point 138° C.) was used in place of ethylbenzene.

(2) Polymerization of Ethylene

Ethylene was polymerized in the same manner as in Example 1 (2) except that methylaluminoxane obtained in (1) above was used as the aluminoxane. As a result, 102 g of polyethylene was obtained. Polymerization activity was 224 kg/g Zr.

(3) Polymerization of Styrene

Styrene was polymerized in the same manner as in Example 1 (3) except that methylaluminoxane obtained in (1) above was used as the aluminoxane. As a result, 88.1 g of a polymer was obtained. Polymerization activity was 92.0 kg/g.Ti. Syndiotacticity in racemi pentad of the polymer as determined by a $^{13}$C-NMR analysis was 97%. The results are shown in Table 2.

EXAMPLE 7

(1) Preparation of Aluminoxane

Aluminoxane (methylaluminoxane) was prepared in the same manner as in Example 5 (1) except that as the additional solvent, xylene (boiling point 137° to 144° C.) was used in place of ethylbenzene.

(2) Polymerization of Ethylene

Ethylene was polymerized in the same manner as in Example 1 (2) except that methylaluminoxane obtained in (1) above was used as the aluminoxane. As a result, 115 g of polyethylene was obtained. Polymerization activity was 252 kg/g Zr.

(3) Polymerization of Styrene

Styrene was polymerized in the same manner as in Example 1 (3) except that methylaluminoxane obtained in (1) above was used as the aluminoxane. As a result, 89.4 g of a polymer was obtained. Polymerization activity was 93.4 kg/g.Ti. Syndiotacticity in racemi pentad of the polymer as determined by a $^{13}$C-NMR analysis was 98%. The results are shown in Table 2.

EXAMPLE 8

(1) Preparation of Aluminoxane

Aluminoxane (methylaluminoxane) was prepared in the same manner as in Example 5 (1) except that as the additional solvent, isopropylbenzene (boiling point 152° C.) was used in place of ethylbenzene.

(2) Polymerization of Ethylene

Ethylene was polymerized in the same manner as in Example 1 (2) except that methylaluminoxane obtained in (1) above was used as the aluminoxane. As a result, 118 g of polyethylene was obtained. Polymerization activity was 259 kg/g.Zr.

(3) Polymerization of Styrene

Styrene was polymerized in the same manner as in Example 1 (3) except that methylaluminoxane as obtained in (1) above was used as the aluminoxane. As a result, 90.5 g of a polymer was obtained. Polymerization activity was 94.5 kg/g.Ti. Syndiotacticity in racemi pentad of the polymer as determined by a $^{13}$C-NMR analysis was 97%. The results are shown in Table 2.

COMPARATIVE EXAMPLE 2

(1) Preparation of Aluminoxane

Aluminoxane (methylaluminoxane) was prepared in the same manner as in Example 5 (1) except that as the additional solvent, benzene (boiling point 80° C.) was used in place of ethylbenzene.

(2) Polymerization of Ethylene

Ethylene was polymerized in the same manner as in Example 1 (2) except that methylaluminoxane obtained in (1) above was used as the aluminoxane. As a result, 90 g of a polymer was obtained. Polymerization activity was 197 kg/g.Zr.

(3) Polymerization of Styrene

Styrene was polymerized in the same manner as in Example 1 (3) except that methylaluminoxane obtained in (1) above was used as the aluminoxane. As a result, 15.3 g of a polymer was obtained. Polymerization activity was 16.0 kg/g.Ti. Syndiotacticity in racemi pentad of the polymer as determined by a $^{13}$C-NMR analysis was 96%. The results are shown in Table 2.

EXAMPLE 10

Low Degree Polymerization of Propylene

In a 1-liter autoclave, 400 ml of toluene, 6 mmol as an aluminum atom of methylaluminoxane as obtained in Example 1 (1), and 0.01 mmol of bis(pentamethylcyclopentadienyl)hafnium dichloride were placed succesively in this order, and the temperature was raised to 50° C. Then, hydrogen was introduced so that the hydrogen partial pressure was 1 kg/cm$^2$G, and further propylene was continuously introduced. While maintaining the propylene partial pressure at 8 kg/cm$^2$, the reaction was conducted at a temperature of 50° C. for 4 hours. After the completion of the reaction, the product was washed with 150 ml of a 3N aqueous hydrochloric acid solution to obtain 209.8 g of a propylene low polymer.

Distillation of the polymer thus obtained showed that the polymer contained a dimer fraction (boiling point 53.9° C.) comprising 4-methylpentene-1 having a purity of at least 99%, a trimer fraction (boiling point 129° C.) comprising 4,6-dimethylheptene-1, a tetramer fraction (boiling point 189° C.) comprising 4,6,8-trimethylnonene-1, a pentamer fraction (boiling point 230° C.) comprising 4,6,8,10-tetramethyl-undecene-1, and a fraction comprising hexamer and more monomers.

EXAMPLE 11

(1) Preparation of Aluminoxane

Aluminoxane (methylaluminoxane) was prepared in the same manner as in Example 1 (1) except that a mixture of toluene (boiling point 111° C.) and ethylbenzene (boiling point 136° C.) (weight ratio of the mixture; former:latter = 1:1) was used in place of ethylbenzene.

(2) Polymerization of Ethylene

Ethylene was polymerized in the same manner as in Example 1 (2) except that methylaluminoxane obtained in (1) above was used as the aluminoxane. As a result, 132 g of polyethylene was obtained. Polymerization activity was 289 kg/g.Zr.

(3) Polymerization of Styrene

Styrene was polymerized in the same manner as in Example 1 (3) except that methylaluminoxane obtained in (1) above was used as the aluminoxane As a result, 91.4 g of a polymer was obtained. Polymerization activity was 95.4 kg/g.Ti. Syndiotacticity in racemi pentad of the polymer as determined by a $^{13}$C-NMR analysis was 97%. The results are shown in Table 1.

TABLE 2

| | | Additional Solvent | | | | | |
| --- | --- | --- | --- | --- | --- | --- | --- |
| | Type | Boiling Point (°C.) | Yield of Polyethylene (g) | Polyethylene Activity (kg/g · Zr) | Yield of SPS* (g) | SPS* Activity (kg/g · Ti) | Tacticity (%) |
| Example 5 | Ethylbenzene | 136 | 109 | 239 | 86.7 | 90.5 | 97 |
| Example 6 | p-Xylene | 138 | 102 | 224 | 88.1 | 92.0 | 97 |
| Example 7 | Xylene | 137–144 | 115 | 252 | 89.4 | 93.4 | 98 |
| Example 8 | Isopropylbenzene | 152 | 118 | 259 | 90.5 | 94.5 | 97 |
| Comparative Example 2 | Benzene | 80 | 90 | 197 | 15.3 | 16.0 | 96 |

*SPS: Syndiotactic polystyrene

EXAMPLE 9

Copolymerization of Ethylene and Propylene

In a 1-liter autoclave, 400 ml of toluene, 1 mmol as an aluminum atom of methylaluminoxane obtained in Example 1 (1), and 5 μmol of bis(cyclopentadienyl)zirconium monochloride monohydride were placed successively in this order, and the temperature was raised to 50° C. Then, propylene and ethylene were continuously introduced into the autoclave in the proportions that the propylene partial pressure was 8 kg/cm$^2$ and the ethylene partial pressure was 1 kg/cm$^2$, and the polymerization reaction was conducted at 50° C. for 40 minutes. After the completion of the reaction, the solvent was distilled away, and the product was subjected to de-ashing and washing with diluted hydrochloric acid-methanol and vacuum dried to obtain 42.7 g of a copolymer. Copolymerization activity was 93.6 kg/g.Zr. The copolymer thus obtained was an ethylene-propylene copolymer having a propylene content of 41 mol%.

What is claimed is:

1. A process for preparing aluminoxane which comprises reacting an organoaluminum compound and water in a solvent having a higher boiling point than that of the organoaluminum compound to form a resulting reaction mixture having an initial weight, and condensing the resulting reaction mixture under reduced pressure until the weight of the resulting mixture becomes 1/1.5 to 1/100 of the initial weight.

2. The process as claimed in claim 1, wherein the organoaluminum compound is an organic compound represented by the general formula: $AlR^1_3$ 1 (wherein $R^1$ is an alkyl group having 1 to 8 carbon atoms).

3. The process as claimed in claim 1, wherein the organoaluminum compound is trimethylaluminum, triethylaluminum or triisobutylaluminum.

4. The process as claimed in claim 1, wherein the solvent is aromatic hydrocarbon or aliphatic hydrocarbon.

5. The process as claimed in claim 1, wherein the organoaluminum compound is trimethylaluminum and the solvent is aromatic hydrocarbon.

6. The process as claimed in claim 1, wherein the reaction mixture is condensed until the weight of the resulting mixture becomes ½ to 1/10 of the initial weight.

7. A process for preparing aluminoxane which comprises reacting an organoaluminum compound and water in a solvent system containing a solvent having a higher boiling point than that of the organoaluminum compound to form a resulting reaction mixture having an initial weight, and condensing the resulting reaction mixture under reduced pressure until the weight of the resulting mixture becomes 1/15 to 1/100 of the initial weight and wherein the solvent system is a mixture of not less than 10% by weight of a solvent having a higher boiling point than that of the organoaluminum compound and a solvent having a lower boiling point than that of the organoaluminum compound.

8. A process for preparing aluminoxane which comprises reacting an organoaluminum compound and water, adding a solvent system containing solvent having a higher boiling point than that of the organoaluminum compound to the above obtained reaction mixture to form a solution having an initial weight, and condensing the resulting solution under reduced pressure until the weight of the resulting solution becomes 1/1.5 to 1/100 of the initial weight.

9. The process as claimed in claim 8, wherein the organoaluminum compound is an organic compound represented by the general formula: $AlR^1_3$ (wherein $R^1$ is an alkyl group having 1 to 8 carbon atoms).

10. The process as claimed in claim 8, wherein the organoaluminum compound is trimethylaluminum, triethylaluminum or triisobutylaluminum.

11. The process as claimed in claim 8, wherein the solvent is aromatic hydrocarbon or aliphatic hydrocarbon.

12. The process as claimed in claim 8, wherein the organoaluminum compound is trimethylaluminum and the solvent is aromatic hydrocarbon.

13. The process as claimed in claim 8, wherein the reaction mixture is condensed until the weight of the resulting solution becomes ½ to 1/10 of the initial weight.

14. The process as claimed in anyone of claim 8 to 13, wherein the solvent system is a mixture of not less than 10% by weight of a solvent having a higher boiling point than that of the organoaluminum compound and a solvent having a lower boiling point than that of the organoaluminum compound.

15. The process of claim 1, wherein the solvent is an aliphatic hydrocarbon.

16. The process of claim 1, wherein the solvent is propylbenzene or cumene.

17. The process of claim 1 wherein the solvent is octane, nonane or decane.

18. The process of claim 1, 7 or 8 wherein the solvent is ethylbenzene.

19. The process of claim 1, 7 or 8 wherein the solvent is xylene or p-xylene.

20. The process of claim 1, 7 or 8 wherein the solvent is isopropyl benzene.

21. The process of claim 7 wherein the reaction mixture is condensed until a weight of the resulting mixture becomes ½ to 1/10.

22. A process for preparing aluminoxane which comprises reacting an organoaluminum compound and water in a solvent system containing solvent having a higher boiling point than that of the organoaluminum compound, and condensing the resulting reaction mixture under atmospheric pressure or reduced pressure and wherein the solvent system is a mixture of not less than 10% by weight of a solvent having a higher boiling point than that of the organoaluminum compound and a solvent having a lower boiling point than that of the organoaluminum compound.

* * * * *